(12) United States Patent
Beaupré et al.

(10) Patent No.: US 7,530,986 B2
(45) Date of Patent: May 12, 2009

(54) LAMINATED ULTRASONIC END EFFECTOR

(75) Inventors: Jean M. Beaupré, Cincinnati, OH (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 213 days.

(21) Appl. No.: 09/757,013

(22) Filed: Jan. 8, 2001

(65) Prior Publication Data

US 2002/0091404 A1    Jul. 11, 2002

(51) Int. Cl.
*A61B 17/32* (2006.01)
*A61B 17/34* (2006.01)

(52) U.S. Cl. .................................. 606/169; 606/185

(58) Field of Classification Search .............. 606/166, 606/169–171, 181, 184, 185, 187, 190, 176–178; 604/22; 30/144, 346.56, 355, 340, 341, 342, 30/329, 337
See application file for complete search history.

(56) References Cited

U.S. PATENT DOCUMENTS

| 2,784,751 | A | * | 3/1957 | Alexander | 30/394 |
|---|---|---|---|---|---|
| 2,930,912 | A | | 3/1960 | Miller | |
| 3,053,124 | A | | 9/1962 | Balamuth et al. | |
| 4,406,284 | A | * | 9/1983 | Banko | 606/169 |
| 4,622,966 | A | * | 11/1986 | Beard | 606/28 |
| 4,784,034 | A | * | 11/1988 | Stones et al. | 83/852 |
| 4,802,476 | A | * | 2/1989 | Noerenberg et al. | 606/48 |
| 4,911,161 | A | | 3/1990 | Schechter | |
| 4,992,048 | A | | 2/1991 | Goof | |
| 5,057,182 | A | | 10/1991 | Wuchinich | |
| 5,242,385 | A | * | 9/1993 | Strukel | 604/22 |
| 5,448,831 | A | * | 9/1995 | Harwood | 29/890.08 |
| 5,935,143 | A | * | 8/1999 | Hood | 606/169 |
| 6,228,046 | B1 | * | 5/2001 | Brisken | 604/22 |
| 6,887,252 | B1 | * | 5/2005 | Okada et al. | 606/169 |
| 2001/0031964 | A1 | * | 10/2001 | Gentelia et al. | 606/45 |
| 2005/0273127 | A1 | * | 12/2005 | Novak et al. | 606/169 |

FOREIGN PATENT DOCUMENTS

| EP | 0 968684 A1 | 1/2000 |
|---|---|---|
| EP | 0 970660 A1 | 1/2000 |
| GB | 145691 | 7/1921 |
| GB | 868784 | 5/1961 |

\* cited by examiner

*Primary Examiner*—Justine R Yu
*Assistant Examiner*—Shumaya B Ali

(57) ABSTRACT

A laminated ultrasonic waveguide and a method of fabrication thereof including stamping at least two pieces of sheet stock to form stamped parts of the laminated ultrasonic waveguide. The stamped parts are then laminated together to form a laminated ultrasonic waveguide for transferring ultrasonic acoustic energy along a longitudinal axis of the laminated ultrasonic waveguide. The laminated ultrasonic waveguide may be part of an ultrasonic surgical instrument having an active tip end-effector, which is placed in contact with tissue of a patient to couple ultrasonic energy transferred along the laminated ultrasonic waveguide to the tissue. The stamped pieces of sheet stock can also be stamped to form one or more channels extending along the length of the laminated ultrasonic waveguide. The laminated ultrasonic waveguide can also define a connector at a proximal end thereof to transfer ultrasonic energy into the laminated ultrasonic waveguide. In different embodiments, the laminated ultrasonic waveguide comprises first and second (and third or more) stamped pieces of sheet stock that are laminated together.

12 Claims, 2 Drawing Sheets

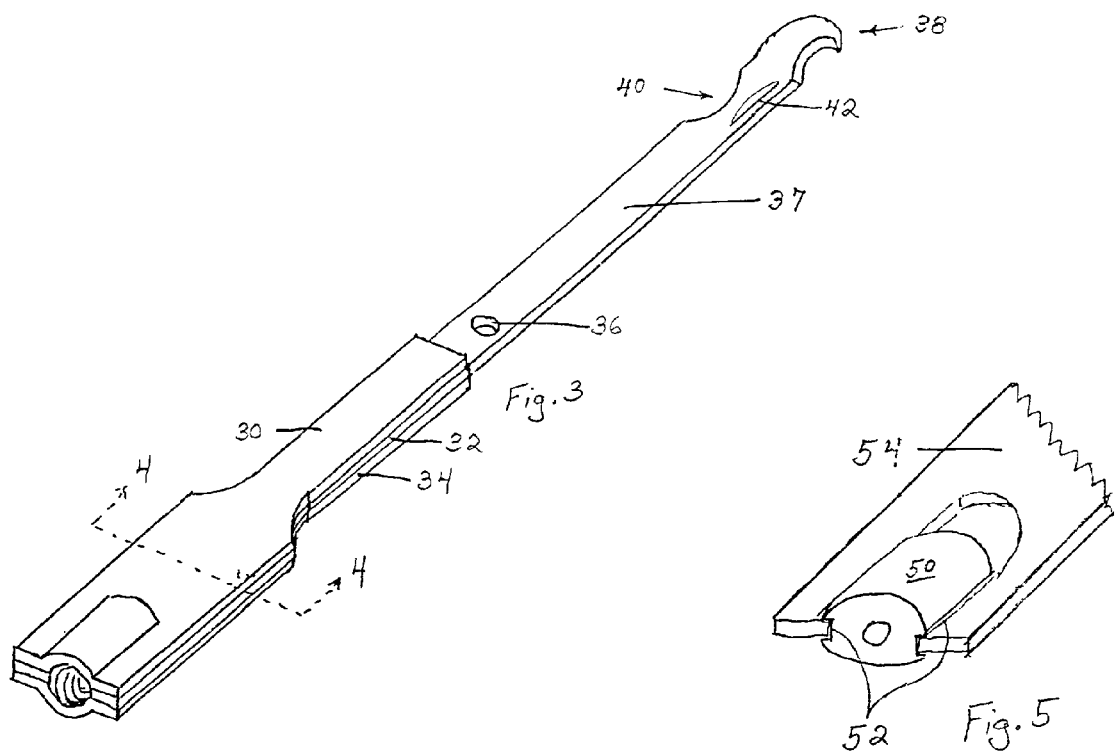
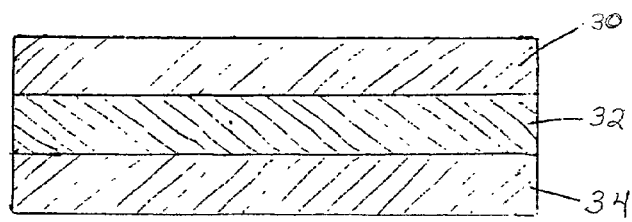

LAMINATED ULTRASONIC END EFFECTOR

BACKGROUND OF THE INVENTION

1. Field of the Invention

The present invention relates generally to laminated ultrasonic waveguides fabricated from sheet stock and a method of fabrication thereof, and more particularly pertains to laminated ultrasonic waveguides or blades fabricated from sheet metal stock and a method of fabrication thereof which extend the possible geometries of the ultrasonic waveguides or blades while reducing manufacturing costs and material waste.

2. Discussion of the Prior Art

Ultrasonic waveguides are utilized in many different technical fields, such as in ultrasonic medical instruments, including both hollow core and solid core instruments, which are well known in the art and are used for the safe and effective treatment of many medical conditions. Ultrasonic instruments, and particularly solid core ultrasonic instruments, are advantageous because they may be used to cut and/or coagulate organic tissue using energy in the form of mechanical vibrations at ultrasonic frequencies transmitted to a surgical end-effector. Ultrasonic vibrations, when transmitted to organic tissue at suitable energy levels using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through an ultrasonic waveguide (also known as a blade) to the surgical end-effector. Such instruments are particularly well suited for use in minimally invasive procedures, such as endoscopic or laparoscopic procedures, wherein the end-effector is passed through a trocar to reach the surgical site.

Ultrasonic surgical instruments and devices typically comprise an ultrasonic transducer which converts an electrical signal to oscillatory motion, an ultrasonic waveguide, and an end-effector which amplifies this motion and applies it to tissue being operated on. Ultrasonic vibration is induced in the surgical end-effector, for example, by electrically exciting a transducer which may be constructed of one or more piezoelectric or magnetostrictive elements in the instrument handpiece. Vibrations generated by the transducer section are transmitted to the surgical end-effector via an ultrasonic waveguide or blade extending from the transducer section to the surgical-end effector.

The ultrasonic waveguide or blade is typically formed as a solid core shaft which is machined from a monolithic piece of a titanium or aluminum alloy. If the device is constructed with multiple parts, the multiple parts are joined at antinodes, which are points of low vibrational stress, with joints extending substantially perpendicular to the longitudinal axis of the device. These devices are usually machined from larger pieces of metal, making them quite expensive to manufacture.

Reducing features and/or stock size can reduce the amount of machining required to form an ultrasonic waveguide or blade. However, most machining is performed on a lathe, such that the material and amount of machining is dictated by the maximum feature size. An ultrasonic waveguide or blade with a 1 cm lateral feature would generally require stock with a minimum of 2 cm diameter, even if the final part is only a few millimeters thick at any point. Moreover, any internal features of the ultrasonic waveguide or blade must be created with "line of sight" methods (i.e., drilled holes are possible, but S-shaped channels are not).

SUMMARY OF THE INVENTION

Accordingly, it is a primary object of the present invention to provide laminated ultrasonic waveguides fabricated from sheet stock and a method of fabrication thereof.

A further object of the subject invention is the provision of laminated ultrasonic waveguides or blades fabricated from sheet metal stock and a method of fabrication thereof which extend the possible geometries of the ultrasonic waveguides or blades while reducing manufacturing costs and material waste. The possible geometries can include features such as channels for irrigation, suction, cooling, damping and threaded connections.

Pursuant to the present invention, ultrasonic waveguides or blades are fabricated from multiple (two, three, four or more) layers of sheet stock, preferably of a titanium or aluminum alloy, to produce a laminated structure. This allows the use of cheaper manufacturing methods including stamping with a die. Structures equivalent to those produced in monolithic machined parts are possible using ribs, notches, holes, and other features which are easily formed by stamping. Stamping can produce large quantities of parts with complex geometries (potentially internal in this case) at little per-piece cost and minimal material waste.

Sheet stock ultrasonic waveguides or blades generally require a high degree of symmetry to operate and function correctly. If a threaded attachment feature is added, it requires that the sheet metal be bent into a U shape. If the resulting structure is not welded, the U adds a high degree of asymmetry, reducing the functionality of the ultrasonic waveguide or blade. If two or more layers of sheet stock are used to fabricate an ultrasonic waveguide or blade, symmetry can be maintained and improved while also providing a simple connection method. In addition, ribs can be added to adjust lateral stiffness and transverse modes of the structure.

The present invention allows an ultrasonic waveguide or blade to be constructed much cheaper than a conventional machined waveguide or blade. In addition, features can be stamped into the interior surfaces of the individual pieces to produces channels for suction, irrigation, cooling, damping, threads, etc. which are frequently very difficult to produce in machined parts.

The present invention uses sheet stock instead of billet or rod stock to fabricate ultrasonic waveguides, and results in,
  reduced material waste,
  fewer manufacturing operations,
  reduced piece cost (one time die cost),
  a potential high degree of axial symmetry with or without planar symmetry,
  can produce complex internal structures,
  uses thinner sheet stock than single layer devices which reduces tooling costs,
  provides an ability to add additional laminate layers or even blade tips to modify designs to meet market needs, and
  provides a possible integrated connection feature and method.

In accordance with the teachings herein, the present invention provides a laminated ultrasonic waveguide and a method of fabrication thereof which comprises stamping at least two pieces of sheet stock to form stamped parts of the laminated ultrasonic waveguide. The stamped parts are then laminated together to form a laminated ultrasonic waveguide for transferring ultrasonic acoustic energy along a longitudinal axis of the laminated ultrasonic waveguide.

In several disclosed embodiments, the laminated ultrasonic waveguide is part of an ultrasonic surgical instrument having an active tip end-effector which is placed in contact with tissue of a patient to couple ultrasonic energy transferred along the laminated ultrasonic waveguide to the tissue. The stamped pieces of sheet stock can also be stamped to form one or more channels extending along the length of the laminated ultrasonic waveguide. Moreover, a distal portion of each of the stamped pieces of sheet stock can have a longitudinal rib stamped therein to provide lateral stiffness for the laminated ultrasonic waveguide.

However, it should be realized that the laminated ultrasonic waveguides of the present invention could also be used in many other diverse applications.

The laminated ultrasonic waveguide can also define a connector at a proximal end thereof to transfer ultrasonic energy into the laminated ultrasonic waveguide.

In one embodiment, the laminated ultrasonic waveguide comprises first and second stamped half pieces of sheet stock which are laminated together. Each of the stamped first and second half pieces of sheet stock defines half of a cylindrical connector at a proximal end of the laminated ultrasonic waveguide which has threads stamped into an interior surface thereof, such that the first and second half pieces define a cylindrical connector having threads on the interior surface thereof for providing a threaded connector to the laminated ultrasonic waveguide.

In another embodiment, the ultrasonic waveguide comprises first outer, second inner and third outer stamped pieces of sheet stock which are laminated together. Each of the first, second and third stamped pieces of sheet stock defines a portion of a cylindrical connector at a proximal end of the laminated ultrasonic waveguide which has threads stamped into an interior surface thereof, such that the first, second and third stamped pieces define the cylindrical connector having threads stamped into the interior surface thereof for providing a threaded connector to the laminated ultrasonic waveguide.

In a farther embodiment, the first and third outer laminated pieces of sheet stock extend from the proximal end of the ultrasonic waveguide for a portion of the length thereof, and the second inner laminated piece of sheet stock extends for the full length of the ultrasonic waveguide from the proximal end of the ultrasonic waveguide to a distal active tip end thereof. The second inner laminated piece can also form an end-effector at the distal end of the ultrasonic laminated waveguide.

In one alternative embodiment, a piece of sheet stock is mounted and secured to longitudinally extending slots in an outer circumference of a separate threaded connector.

BRIEF DESCRIPTION OF THE DRAWINGS

The foregoing objects and advantages of the present invention for laminated ultrasonic waveguides fabricated from sheet stock may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 3 illustrates a further embodiment fabricated from three layers of sheet stock.

FIG. 4 is a cross section of the device in FIG. 3 taken along arrows 4-4 in FIG. 3 and illustrates the laminated construction of the ultrasonic waveguide.

FIG. 5 illustrates an alternate embodiment wherein a stamped sheet stock piece ultrasonic waveguide is coupled to an alternate threaded connector having opposed longitudinal slots in which the stamped sheet stock piece is positioned and secured.

DETAILED DESCRIPTION OF THE INVENTION

Figure 1:
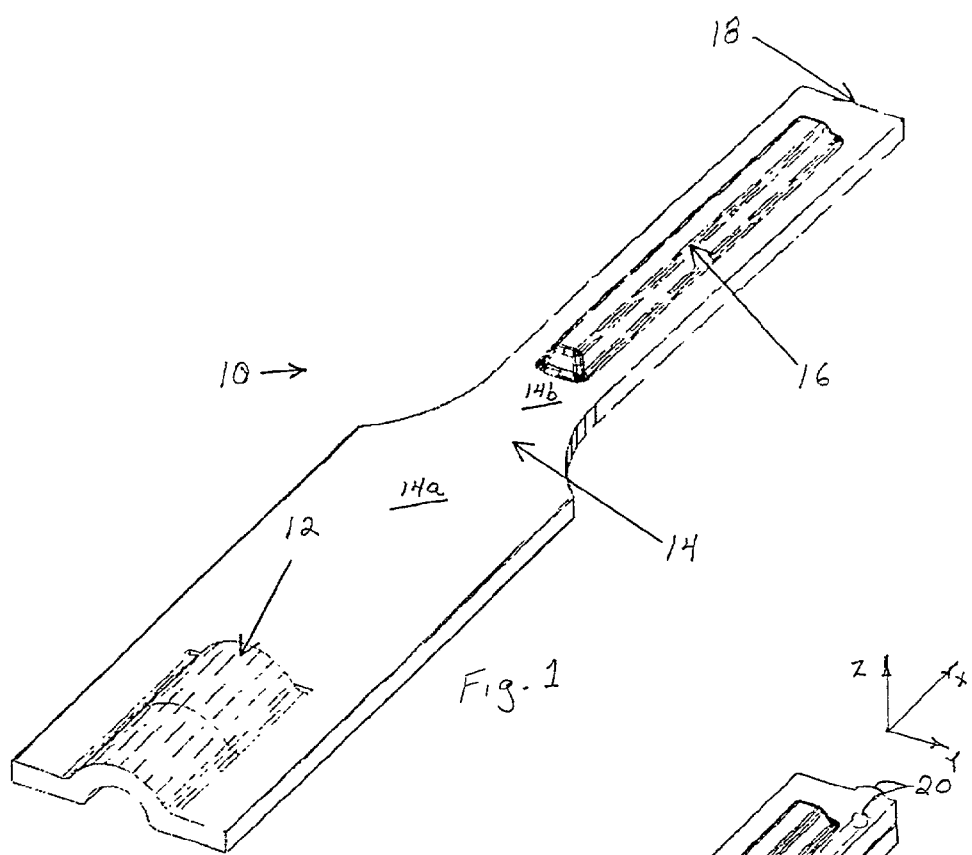
FIG. 1 illustrates an individual stamped sheet stock piece, wherein two or more similar pieces are laminated together to produce an ultrasonic waveguide or blade.

An ultrasonic surgical system typically includes an ultrasonic generator, a handpiece assembly, and an acoustic transmission assembly terminating in an end-connector. An electrical signal at a selected amplitude, frequency and phase drives one or more piezoelectric elements of the acoustic assembly, thereby converting the electrical energy into longitudinal waves of ultrasonic energy which propagate through an ultrasonic waveguide in the acoustic assembly in an acoustic standing wave to vibrate the acoustic assembly at a selected frequency and amplitude. The end-effector at the distal end of the acoustic assembly is placed in contact with tissue of the patient to transfer the ultrasonic energy to the tissue.

As the end-effector couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation varies with the vibrational amplitude of the end-effector, the amount of pressure applied by the user, and the sharpness of the end-effector. The end-effector tends to focus the vibrational energy onto the tissue in contact therewith, intensifying and localizing thermal and mechanical energy delivery. The end-effector may also include a non-vibrating clamp arm assembly to, for example, grip tissue or compress tissue against the ultrasonic tool.

The end-effector may be formed integral with the acoustic ultrasonic waveguide as a single unit, or may alternately be connected to the waveguide by a threaded connection, or by a welded joint, preferably at or near an antinode.

The ultrasonic waveguide or blade may have a length substantially equal to an integral multiple of one-half the system wavelength ($n\lambda/2$). The distal end of the ultrasonic waveguide or blade is preferably disposed near an antinode in order to provide the maximum longitudinal excursion of the distal end and to tune the acoustic assembly to a preferred resonant frequency when the acoustic assembly is not loaded by tissue. When the transducer assembly is energized, the distal end of the ultrasonic waveguide or blade is configured to move in the range of, for example, approximately 10 to 500 microns peak-to-peak, preferably in the range of about 30 to 150 microns, and most preferably at about 90 microns at a predetermined vibrational frequency.

Pursuant to the present invention, the ultrasonic waveguide or blade is constructed of multiple (two, three, four or more) laminations of sheet stock or sheet foil material which propagate ultrasonic energy efficiently, such as a titanium alloy (e.g., Ti-6Al-4V) or an aluminum alloy, or may be fabricated from any other suitable ultrasonically efficient material. It is also contemplated that the ultrasonic waveguide or blade may have a surface treatment to improve the delivery of energy and the desired tissue effect. For example, the ultrasonic waveguide or blade may be micro-finished, coated, plated, etched, grit-blasted, roughened or scored to enhance coagulation and cutting of tissue and/or reduce adherence of tissue and blood to the end-effector. Additionally, the end-effector may be sharpened or shaped to enhance its characteristics. For example, the end-effector may be blade shaped, hook shaped, or ball shaped.

The end-effector can provide a multitude of edges and surfaces designed to provide a multitude of tissue effects: clamped coagulation, clamped cutting, grasping, back-cutting, dissection, spot coagulation, tip penetration and tip scoring.

Figure 2:
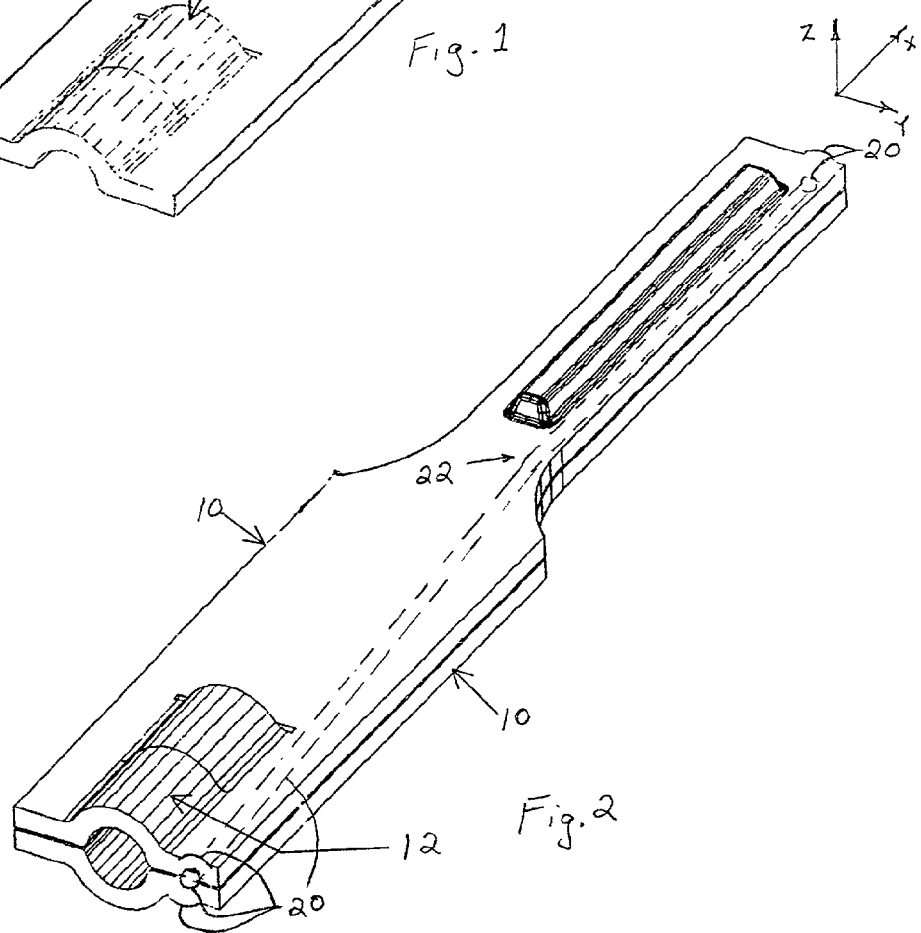
FIG. 2 shows two sheet stock parts as shown in FIG. 1 bonded back to back to form a laminated structure.

Referring to the drawings in detail, FIG. 1 illustrates an individual stamped sheet stock piece 10. Pursuant to the teachings of the present invention, two or more similar pieces 10 are laminated together, as illustrated in FIG. 2, to produce an ultrasonic waveguide or blade. The stamped sheet stock 10 has a connection feature 12, an amplification feature 14, a rib 16 which is provided for lateral stiffness and frequency tuning, and an active tip 18. In FIG. 1, the active tip 18 is a simple square end, however in alternative embodiments any suitable end-effector, such as a blade, hook, ball, curve, point, etc. which meets the resonant requirements of the instrument is possible, as is well known to practitioners of the art.

The amplification feature 14 of the ultrasonic waveguide includes a distal region 14b having a smaller cross-section area than a proximal region 14a thereof, thereby forming a vibrational amplitude step-up junction. The step-up junction acts as a velocity transformer as is known in the art, increasing the magnitude of the ultrasonic vibration transmitted from the proximal region 14a to the distal region 14b of the ultrasonic waveguide.

FIG. 2 shows two sheet stock parts 10, 10 as shown in FIG. 1 which are bonded back to back to form a laminated ultrasonic waveguide structure. Any suitable bonding method can be used such as adhesives, spot welding, laser welding, or any suitable alternative bonding method. If threads are stamped or coined into the interior surfaces of the parts 10 at the connection feature 12, the component is now a complete and functional device. FIG. 2 also illustrates an x, y, z coordinate system. The device may have lateral symmetry about the x-y plane and about the x-z plane as shown, but will always have axial symmetry along the longitudinal x axis which is more critical. The stamped sheet stock parts 10,10 are generally stamped and produced by the same die, and any flaws such as burrs produced by the die will be reproduced in each stamped sheet stock part 10, 10. Therefore, burrs and other flaws in one stamped part 10 will be balanced by an identical flaw diametrically opposite thereto in the second stamped part 10. The two parts 10,10 do not need to be identical, but identical parts provide a symmetry advantage.

FIG. 2 also illustrates a channel 20 which has been stamped into each of the sheet stock parts 10 which extends from the proximal end to the distal end of the ultrasonic waveguide, such that it can be used for suction, irrigation, cooling, etc. The channel 20 has a bend at 22, such that the channel 20 is not a "line of sight" feature. In alternative embodiments, several channels extending parallel to the longitudinal axis of the waveguide may be provided for different purposes.

Additional layers may be laminated on top of or between the two sheet parts 10,10 shown in FIG. 2 to provide an additional thickness or additional features. FIG. 3 illustrates a further embodiment fabricated from three layers 30, 32, 34 of sheet stock. FIG. 3 also illustrates other possible variations of design which are possible using the techniques of the present invention, including three or more layers 30, 32, 34, holes 36, and a single layer section 37 extending to an end-effector 38. A single layer may be used in some sections of the ultrasonic waveguide, such as when a thinner end-effector curved cutting tip 38 is needed, as illustrated in FIG. 3. In different embodiments, the single layer 37 can extend for the full length of the ultrasonic waveguide, or in other embodiments can extend for a partial length thereof.

When the distal end of the ultrasonic waveguide is not axially symmetrical, as is the case with the curved cutting tip 38, the ultrasonic waveguide can also include a balance region located between the end-effector and a balance node. The balance region can include an asymmetric balance feature by selectively removing (at 40) or adding (at 42) mass from or to the balance region, as disclosed and taught in U.S. application Ser. Nos. 106,661 and 106,686, filed on Jun. 28, 1998.

FIG. 4 is a cross section of the device in FIG. 3 taken along arrows 4-4 in FIG. 3, and illustrates the laminated construction of the ultrasonic waveguide.

FIG. 5 illustrates an alternate embodiment having an alternate threaded connector 50 with opposed longitudinal slots 52 in which a single sheet stock piece 54 is positioned and secured. The single sheet stock piece 54 would then be laminated together with other stamped sheet stock pieces as illustrated in the other embodiments herein.

While several embodiments and variations of the present invention for laminated ultrasonic blades fabricated from sheet stock are described in detail herein, it should be apparent that the disclosure and teachings of the present invention will suggest many alternative designs to those skilled in the art.

What is claimed is:

1. A laminated ultrasonic end effector having a distal end and a proximal end and comprising at least two stamped pieces of sheet stock which are laminated together and at least one lumen extending from the distal end to the proximal end and wherein first and second stamped pieces of sheet stock are laminated together, and each of the stamped first and second pieces of sheet stock defines half of a cylindrical connector at a proximal end of the laminated ultrasonic end effector which has threads stamped into an interior surface of each half cylindrical connector, such that the first and second half pieces define a cylindrical connector having threads on the interior surface thereof providing a threaded connector connecting to an acoustic transmission assembly.

2. The laminated ultrasonic end effector of claim 1, wherein the laminated ultrasonic end effector defines a connector at a proximal end of the laminated ultrasonic end effector to receive ultrasonic energy from an acoustic transmission assembly.

3. The laminated ultrasonic end effector of claim 1, wherein a distal portion of each of the stamped pieces of sheet stock has a longitudinal rib stamped therein extending along the longitudinal axis of the laminated ultrasonic end effector to provide lateral stiffness for the laminated ultrasonic end effector.

4. The ultrasonic waveguide of claim 1, wherein a piece of sheet stock is mounted and secured to longitudinally extending slots in an outer circumference of a separate threaded connector.

5. A method of fabricating a laminated ultrasonic end effector having a distal end and a proximal end comprising stamping and forming at least two stamped pieces of sheet stock to form parts of the body of the laminated ultrasonic end effector and at least one lumen extending from the distal end to the proximal end, and laminating together the at least two stamped pieces of sheet stock to form the body of the laminated ultrasonic end effector and further including stamping and forming first and second pieces of sheet stock while defining in each of the stamped first and second pieces of sheet stock half of a cylindrical connector at a proximal end of the laminated ultrasonic end effector by stamping threads into an interior surface of each half of the cylindrical connector, such that the first and second half pieces define a cylindrical connector having threads on the interior surface thereof providing a threaded connector connecting to the laminated ultrasonic end effector.

6. The method of claim 5, further comprising fabricating an ultrasonic surgical instrument comprising an acoustic transmission assembly, which coupled to the laminated ultrasonic end effector.

7. The method of claim 5, further comprising defining a connector at a proximal end of the laminated ultrasonic end effector to couple to an acoustic transmission assembly.

8. The method of claim 5, including stamping and forming a longitudinal rib in a distal portion of each of the stamped pieces of sheet stock which extends along a longitudinal axis of the laminated ultrasonic end effector.

9. The method of claim 5, including stamping and forming first outer, second inner and third outer stamped pieces of sheet stock while defining in each of the first, second and third stamped pieces of sheet metal a portion of a cylindrical connector at a proximal end of the laminated ultrasonic waveguide by stamping threads into an interior surface of the cylindrical connector, such that the first, second and third stamped pieces define the cylindrical connector having threads stamped into the interior surface of the cylindrical connector for providing a threaded connector to the ultrasonic end effector.

10. The method of fabricating an ultrasonic surgical instrument of claim 9, including stamping and forming the first and third outer laminated pieces of sheet stock to extend from the proximal end of the laminated ultrasonic end effector for a portion of the length of the laminated ultrasonic end effector.

11. The method of claim 10, including forming the second inner laminated piece of sheet stock to extend to a distal tip end of the laminated ultrasonic end effector.

12. The method of claim 5, including mounting and securing a piece of sheet stock to longitudinally extending slots in an outer circumference of a separate threaded connector.

* * * * *